United States Patent
Reinold et al.

(12)

(10) Patent No.: US 6,254,801 B1
(45) Date of Patent: Jul. 3, 2001

(54) HARDNESS-STABILIZING PERCARBOXYLIC ACID SOLUTIONS, A PROCESS FOR THEIR PREPARATION AND THEIR USE

(75) Inventors: Andreas Reinold, Gründau; Egon Walzer, Maintal, both of (DE)

(73) Assignee: Degussa AG, Frankfurt am Main (DE)

( * ) Notice: Subject to any disclaimer, the term of this patent is extended or adjusted under 35 U.S.C. 154(b) by 0 days.

(21) Appl. No.: 09/274,205

(22) Filed: Mar. 23, 1999

(30) Foreign Application Priority Data

Mar. 23, 1998 (DE) .............................. 198 12 588

(51) Int. Cl.[7] .......................... C01B 15/00; C01B 15/055
(52) U.S. Cl. ................. 252/186.23; 252/186.21; 252/186.26; 510/318
(58) Field of Search ................ 252/186.21, 186.23, 252/186.26; 510/318

(56) References Cited

U.S. PATENT DOCUMENTS

| 3,691,139 | * | 9/1972 | Blumbergs et al. ............. 510/318 X |
| 3,956,159 | * | 5/1976 | Jones ............................... 252/186.26 |
| 4,051,059 | * | 9/1977 | Bowing et al. ................ 252/186.23 |
| 4,083,794 | * | 4/1978 | Lee et al. ........................... 510/318 X |
| 4,579,676 | * | 4/1986 | Bull ............................ 252/186.26 X |
| 5,114,611 | * | 5/1992 | Van Kralingen et al. .. 252/186.26 X |
| 5,296,239 | | 3/1994 | Colery et al. ......................... 424/613 |
| 5,494,488 | * | 2/1996 | Arnoldi et al. .................. 510/318 X |
| 5,545,374 | | 8/1996 | French et al. ........................... 422/28 |
| 5,965,033 | * | 10/1999 | Huss et al. ............................ 210/759 |

FOREIGN PATENT DOCUMENTS

| 96 833 | 4/1973 | (DE) . |
| 2616049 | 10/1977 | (DE) . |
| 0 421 974 B1 | 1/1994 | (EP) . |
| 0688302 | 12/1995 | (EP) . |
| 2 321 301 | 3/1977 | (FR) . |
| WO 93/10088 | 5/1993 | (WO) . |
| WO 94/14321 | 7/1994 | (WO) . |
| WO 97/08100 | 3/1997 | (WO) . |

OTHER PUBLICATIONS

CA:95:6798 abs of Khim–Farm Zh 15(3) pp. 35–38 by Voronkov, 1981.*

* cited by examiner

*Primary Examiner*—Richard D. Lovering
(74) *Attorney, Agent, or Firm*—Pillsbury Winthrop LLP

(57) ABSTRACT

Hardness-stabilizing and scale-preventing aqueous percarboxylic acid solutions contain a hardness stabilizer selected from the group (i) polymers prepared by oxidative polymerization of acrolein or of acrolein and acrylic acid, (ii) polyacrylic acid, (iii) copolymers of acrylic acid and another unsaturated carboxylic acid and (iv) polymaleic acid, wherein the average molecular weight $M_w$ of the hardness stabilizer is in the range 500 to 25000, and the solutions are obtained by adding the hardness stabilizer to a percarboxylic acid solution. Preferred solutions contain a hardness stabilizer (i) with a $M_w$ of 1000 to 15000. The solutions may also contain a surfactant. The solution can be used for controlling microorganisms in aqueous systems, in particular water-circulating systems.

7 Claims, No Drawings

HARDNESS-STABILIZING PERCARBOXYLIC ACID SOLUTIONS, A PROCESS FOR THEIR PREPARATION AND THEIR USE

CROSS REFERENCE TO RELATED APPLICATION

The application is based on German application No. 198 12 588.7, filed Mar. 23, 1998, the entire disclosure of which is incorporated herein by reference.

FIELD OF THE INVENTION

The invention relates to hardness-stabilizing percarboxylic acid solutions containing one or more percarboxylic acids from the group performic acid, peracetic acid and perpropionic acid which contain the carboxylic acids from which these acids are derived, hydrogen peroxide, water and a hardness stabilizer. The invention also provides a process for preparing hardness-stabilizing percarboxylic acid solutions and their use.

BACKGROUND OF THE INVENTION

Percarboxylic acids (peroxycarboxylic acids) such as in particular peracetic acid and performic acid are highly effective microbiocides which are used in a very wide range of different water systems for controlling microorganisms, reference being made, by way of example, to WO 97/08100 and EP 0 688 302. The percarboxylic acids mentioned are especially effective in the form of a so-called aqueous equilibrium percarboxylic acid solution which consists substantially of a percarboxylic acid, the carboxylic acid from which it is derived, hydrogen peroxide and water and may also contain a mineral acid catalyst and conventional active oxygen stabilizers in effective amounts.

In order to satisfy specific application-oriented requirements, additives are added to the percarboxylic acid solutions mentioned, such as wetting agents, emulsifiers, corrosion inhibitors and buffers. Microbiocidal compositions in accordance with WO 93/10088 or WO 94/14321 are based on an equilibrium percarboxylic acid and non-ionic surfactants. A similar composition, but with an anionic surfactant selected from the group alkylbenzene sulfonates, alkyl sulfates and alkane sulfonates instead of the non-ionic surfactant, is disclosed in FR 2 321 301 and DE 26 16 049, wherein the composition in the last-named document also contains a phosphonic acid. A stabilised aqueous peracetic acid solution with increased antimicrobial effect and a reduced corrosive effect contains, according to DD 96833, a buffering agent, wetting agents or emulsifiers, such as alkali metal salts of sulfonated fatty acids, fatty alcohol sulfonates, alkane sulfonates and alkylaryl sulfonates, and organic sequestering agents such as dipicolinic acid and ethylenediamine tetraacetic acid. Finally, thickened percarboxylic acid solutions are known, such as those in accordance with EP 0 421 974 B1, which contain a cross-linked acrylic acid polymer and also a sequestering agent from the group of phosphonic acids and nitrogen-containing carboxylic acids.

In water-circulating systems, there is often the need to simultaneously avoid or reduce problems due to the presence of microorganisms and the production of solid coatings of hardness-producing components. Hitherto, a hardness stabilizer, in particular one from the group of phosphonocarboxylic acids, and an equilibrium peracetic acid have been added, separately, to the circulating system for this purpose. This addition process is costly. Although a solution of an equilibrium peracetic acid and a phosphonocarboxylic acid exhibit the required microbiocidal and hardness-stabilizing effect, the storage stability is inadequate.

SUMMARY OF THE INVENTION

Accordingly, the object of the present invention is to provide an agent which combines both a microbiocidal effect and also a hardness-stabilizing and scale-preventing effect in one agent. At the same time, the agent should have high storage stability.

A hardness-stabilizing percarboxylic acid solution containing one or more percarboxylic acids from the group performic acid, peracetic acid and perpropionic acid, the carboxylic acid(s) from which the peracid(s) is/are derived, hydrogen peroxide, water and a hardness stabilizer from the group comprising (i) polymers prepared by the oxidative polymerization of acrolein or of acrolein and acrylic acid, (ii) polyacrylic acid and(iii)copolymers of acrylic acid and another unsaturated carboxylic acid, in particular maleic acid, and(iv) polymaleic acid, wherein the hardness-stabilizer is not cross-linked, the average molecular weight $M_w$, of the hardness stabilizer is in the range 500 to 25000, in particular 1000 to 15000, and some of the carboxyl groups in the hardness stabilizer may have been converted into percarboxyl groups, has been found.

Preferred hardness-stabilizing percarboxylic acid solutions contain peracetic acid or a combination of peracetic acid and performic acid in a total amount of 0.1 to 15 wt. %, in particular 0.5 to 6 wt. %, as the percarboxylic acid. Since the hardness stabilizers also contain carboxyl groups, some of these may have been converted into percarboxylic acid groups by the hydrogen peroxide which is present. Expediently, the solution is aqueous and has a water content of more than 40 wt. %. The percarboxylic acid, the carboxylic acid from which it is derived, hydrogen peroxide and water are preferably present in the equilibrium state or in the vicinity thereof. The solution according to the invention generally contains 0.01 to 10 wt. % of hardness stabilizer (calculated as 100% strength), preferably 0.5 to 5 wt. %. In addition, other additives which adjust certain additives relating to the particular application, may be present. The following additives may be mentioned, by way of example: surfactants, in particular anionic and non-ionic surfactants with wetting, emulsifying and/or dispersing effects, corrosion prevention agents, buffers, conventional active oxygen stabilizers such as phosphonic acid derivatives, pryridinocarboxylic acids, aminocarboxylic and hydroxycarboxylic acids, tin compounds and free-radical scavengers, and mineral acids for adjusting the equilibrium such as sulfuric acid, phosphoric acid, pyrophosphoric acid and polyphosphoric acid.

The use of aminocarboxylic acids such as ethylenediamine tetraacetic acid (EDTA)and aminophosphonic acids as sequestering agents for trapping heavy metals contained in percarboxylic acid solutions and which reduce the storage stability of active oxygen compound is known per se, but these types of substances are, on the one hand, undesirable in large amounts from an ecotoxicological point of view and/or their hardness-stabilizing effect is inadequate. Moreover, these types of substances are not really suitable as scale-preventers; and a scale-preventer is definitely required in aqueous circulating systems. Hitherto a phosphonocarboxylic acid, in particular 2-phosphonobutane-1,2,4-tricarboxylic acid (PBTC), has been used separately in water-circulating systems in order to control microorganisms and lower forms of plant and animal life and to prevent scaling. The addition of PBTC to an equilibrium peracetic acid leads, however, as shown in comparative tests, to solutions with unsatisfactory storage stability and which are thus not commercially viable. The solutions according to the invention, in contrast, are characterised by high storage stability.

It was also found that equilibrium peracetic acid solutions containing anionic surfactants became very cloudy when diluted with tap water due to the precipitation of lime soaps. This problem can be largely reduced if the solution also contains a hardness stabilizer according to the invention in an effective amount, in addition to the anionic surfactant. These types of percarboxylic acid solutions preferably contain 0.5 to 6 wt. % of peracetic acid or a combination of peracetic acid and performic acid, 1 to 10 wt. %, in particular 1 to 7.5 wt. % of hardness stabilizer according to the invention (calculated as 100% strength), in particular those in accordance with (i) above, and 0 to 5 wt. % of surfactants, in particular anionic surfactants based on sulfonic acid and sulfate esters.

The hardness stabilizers according to the invention contained in the percarboxylic acid solutions act both as hardness stabilizers and also as scale-preventers. Products with $M_w$ less than 500 and greater than 25000 are less suitable because either the effect and/or the solubility are too low. Products with a molecular weight $M_w$ in the range 500 to 15000, in particular 1000 to 10000 are preferred. The class of substances in accordance with (i) comprises carboxyl group-containing polymers, prepared by the polymerization of acrolein, but preferably prepared by the polymerization of acrolein and acrylic acid in the presence of hydrogen peroxide. These types of products are commercially available under the name POC™ (from Degussa AG), for example POC HS2020 with a molecular weight $M_w$ of about 9000. Hardness stabilizers in accordance with (ii) are polyacrylic acids and optionally modified polyacrylic acids, preferably those with an average molecular weight $M_w$ of about 1000 to 10000. Copolymers based on acrylic acid with another olefinic carboxylic acid, wherein at least one carboxyl group is preferably bonded to an olefinic carbon atom, such as maleic acid and polymaleic acid, are also suitable, if $M_w$ is in the preferred range of 500 to 15000. Hardness stabilizers in accordance with (i), (ii), (iii) and (iv) may contain a small amount of lower carboxylic acids and/or traces of acrylic acid, as a result of their method of preparation. The polymers to be used as hardness stabilizers should be substantially non-crosslinked and lead to no noticeable thickening of the percarboxylic acid solution. The viscosities of the solutions according to the invention are generally less than 20 mpa.s.

In addition to the hardness-stabilizing, scale-preventing and turbidity-reducing effects which can be attributed to the hardness stabilizer, the hardness stabilizers to be used are also characterised in that they increase the active oxygen stability of the percarboxylic acid solution.

Percarboxylic acid solutions according to the invention are prepared in the simplest case by adding the hardness stabilizer to a percarboxylic acid solution, in particular an equilibrium percarboxylic acid solution, previously prepared in a conventional manner. A new equilibrium is established by allowing the solution to stand. It is also possible to add the hardness stabilizer to one of the reaction partners before preparing the percarboxylic acid solution, that is the carboxylic acid, the hydrogen peroxide or the water, or a mixture thereof, and to prepare the percarboxylic acid solution from the corresponding solutions.

Percarboxylic acid solutions according to the invention can be used in particular for the prevention and the control of harmful microorganisms such as molds, viruses, bacteria, yeasts and algae, as well as worms, mussels and insects, in aqueous systems, in particular water-circulating systems and for disinfecting surfaces.

DETAILED DESCRIPTION OF THE PREFERRED EMBODIMENTS

Examples E1 to E3 and Comparison Examples CE1 to CE3

Starting from an equilibrium peracetic acid solution with a concentration of 1.91 wt. % of peracetic acid (PAA), 45.08 wt. % of $H_2O_2$ and an active oxygen content (AO) of 21.62 wt. %, mixtures with 5, 15 and 25 wt. % of Bayhibit AM™, a 50 wt. % strength commercial product consisting of 2-phosphono-butane- 1,2,4-tricarboxylic acid from Bayer AG, were prepared (CE1 to CE3). In the same way, mixtures of the peracetic acid solution with 5, 15 and 25 wt. % of POC 2020™, a 50 wt. % strength aqueous solution of a hardness stabilizer in accordance with (i) from Degussa AG, were prepared (E1 to E3).

Establishment of the equilibrium and the stability were determined by determining the concentrations of PAA, $H_2O_2$ and AO; the determinations were performed in a known manner using cerium(IV) sulfate and sodium thiosulfate.

TABLE 1

Mixtures with POC 2020 ™ as hardness stabilizer

| No. | Amount of POC 2020 ™ (wt. %) | Storage time D = days W = weeks | PAA *) (wt. %) | $H_2O_2$ (wt. %) | AO (wt. %) |
|---|---|---|---|---|---|
| E1 | 5 | Start | 2.24 | 44.77 | 21.52 |
| | | 1 D | 2.38 | 44.70 | 21.53 |
| | | 4 D | 2.49 | 44.17 | 21.28 |
| | | 1 W | 2.78 | 44.02 | 21.27 |
| | | 2 W | 2.80 | 44.24 | 21.38 |
| | | 65 W | 2.81 | 42.35 | 20.48 |
| | | 93 W | 2.85 | 41.61 | 20.15 |
| E2 | 15 | Start | 2.69 | 39.49 | 19.44 |
| | | 1 D | 2.85 | 39.47 | 19.16 |
| | | 4 D | 3.18 | 39.11 | 19.06 |
| | | 1 W | 3.39 | 38.79 | 18.96 |
| | | 2 W | 3.99 | 38.76 | 19.06 |
| | | 65 W | 3.77 | 33.70 | 16.62 |
| | | 93 W | 2.79 | 30.27 | 14.89 |
| E3 | 25 | Start | 2.87 | 35.00 | 17.05 |
| | | 1 D | 3.37 | 34.42 | 16.89 |
| | | 4 D | 3.90 | 34.04 | 16.82 |
| | | 1 W | 4.15 | 33.78 | 16.76 |
| | | 2 W | 4.48 | 33.46 | 16.67 |
| | | 65 W | 3.91 | 26.25 | 13.15 |
| | | 93 W | 2.94 | 22.63 | 11.25 |

*) Sum of all percarboxylic acids calculated as peracetic acid

TABLE 2

Mixtures with Bayhibit AM ™ (PBTC) as hardness stabilizer

| No. | Amount of PBTC (wt. %) | Storage time D = days W = weeks | PAA *) (wt. %) | $H_2O_2$ (wt. %) | AO (wt. %) |
|---|---|---|---|---|---|
| CE1 | 5 | Start | 2.25 | 44.64 | 21.45 |
| | | 1 D | 2.29 | 44.52 | 21.41 |
| | | 4 D | 2.38 | 44.19 | 21.28 |
| | | 1 W | 2.60 | 44.38 | 21.43 |
| | | 2 W | 2.69 | 44.34 | 21.42 |
| | | 65 W | 2.29 | 41.39 | 19.92 |
| | | 93 W | 2.15 | 40.21 | 19.34 |
| CE2 | 15 | Start | 2.77 | 39.53 | 19.16 |
| | | 1 D | 2.98 | 39.47 | 19.18 |
| | | 4 D | 3.30 | 39.29 | 19.16 |
| | | 1 W | 3.41 | 38.86 | 18.82 |
| | | 2 W | 3.67 | 39.03 | 19.12 |
| | | 65 W | 2.41 | 30.41 | 14.79 |
| | | 93 W | 1.67 | 25.04 | 12.09 |

TABLE 2-continued

Mixtures with Bayhibit AM ™ (PBTC) as hardness stabilizer

| No. | Amount of PBTC (wt. %) | Storage time D = days W = weeks | PAA *) (wt. %) | $H_2O_2$ (wt. %) | AO (wt. %) |
|---|---|---|---|---|---|
| CE3 | 25 | Start | 3.20 | 34.30 | 16.81 |
|  |  | 1 D | 3.54 | 34.42 | 16.93 |
|  |  | 4 D | 3.81 | 34.09 | 16.80 |
|  |  | 1 W | 4.26 | 33.84 | 16.74 |
|  |  | 2 W | 4.20 | 33.65 | 16.70 |
|  |  | 65 W | 1.23 | 14.95 | 7.28 |
|  |  | 93 W | 0.35 | 5.82 | 2.81 |

*) Sum of all percarboxylic acids, calculated as peracetic acid

The equilibrium becomes established within about 2 weeks after addition of the hardness stabilizer in E1 to E3 and CE1 to CE3. However, the concentration of percarboxylic acid continues to increase slightly after that, evidently due to a reaction between $H_2O_2$ and the carboxyl groups in the hardness stabilizer. The amount of hardness stabilizer added has an effect on the maximum value for the percarboxylic acids. The total concentration of percarboxylic acids after 2 weeks in examples E1 to E3 was somewhat greater than in comparison examples CE1 to CE3. The reason for this is thought to be that some of the carboxyl groups in the POC 2020 used and/or the secondary constituents contained therein were converted into percarboxyl groups.

The solutions according to the invention have a higher active oxygen stability than the solutions in the comparison examples. The lower storage stability of the solutions not according to the invention is demonstrated in particular with higher concentrations of hardness stabilizer.

Example E4 and Comparison Example CE4

The effect of the hardness stabilizer/scale-preventer POC 2020™ in an equilibrium peracetic acid which contained an anionic surfactant was tested on diluting the solution with water with a standardised hardness (21.28° d). An equilibrium peracetic acid with 5 wt. % of PAA (=PAA 5%) was used and the amounts of surfactant Hostapur SAS 60™ (secondary Na alkane sulfonate salt, 60% strength, from Hoechst AG) and POC 2020™ given in the Table were added. The amounts of SAS 60™ and POC 2020™ given in the Table are cited as 100% active substance and with reference to the solution. The solutions were diluted to a PAA concentration of 0.5 wt. % and 1 wt. %. The compositions of the solutions and the turbidity values are given in Table 3.

TABLE 3

|  |  | Turbidity when diluted | |
|---|---|---|---|
| No. | Composition | to 0.5% PM | to 1% PAA |
| CE4 | PAA 5% + 3% SAS 60 | heavy | very heavy |
| E4/1 | PAA 5% + 1% SAS 60 + 1% POC 2020 | slight | moderate |
| E4/2 | PM 5% + 3% SAS 60 + 3% POC 2020 | slight/moderate | moderate |
| E4/3 | PAA 5% + 1% SAS 60 + 3% POC 2020 | very slight | slight |

The degree of turbidity of an anionic surfactant-containing peracetic acid solution, when it is diluted with hard water, can be substantially reduced by adding a hardness stabilizer according to the invention.

Example E5 and Comparison Example CE5

The effect of POC 2020™ as an active oxygen stabilizer in an equilibrium peracetic acid (=E5), as compared with an unstabilized PAA solution and a PAA solution stabilised with different stabilizers, was determined.

Aqueous peracetic acid solutions consisting of 27.9 wt. % of $H_2O_2$, 28.1 wt. % of acetic acid, 2 wt. % of polyphosphoric acid, the appropriate stabilizer and water (to make up to 100%) were prepared. The solutions were stored for 7 days, then a V4A stainless steel plate (material 1.4571) was added to 320 g of each solution, corresponding to a loading of 13 ml/cm². After 14 days, the concentration of PAA and $H_2O_2$ was again determined and the rate of decomposition (140 g, heated for 1 h at 60° C., $O_2$ evolved in 30 min measured) was determined. The results are given in Table 4.

The hardness stabilizers used according to the invention are also suitable as active oxygen stabilizers.

TABLE 4

| No. | Stabilizer *) | Rate of decomposition (ml $O_2$) after 7 Days maturation | Concentrations (wt. %) and rate of decomposition (ml $O_2$) after 14 days storage of mature solutions in the presence of V4A | | |
|---|---|---|---|---|---|
|  |  |  | % PAA | % $H_2O_2$ | ml $O_2$ |
| CE 5/1 | none | n.d. | 15.06 | 21.38 | 3.6 |
| CE 5/2 | with 100 ppm DPA + 400 ppm HEDP | 0.1 | 15.44 | 21.91 | 1.3 |
| E 5/1 | with 100 ppm POC 2020 | 0.6 | 15.31 | 21.26 | 3.0 |
| E 5/2 | with 500 ppm POC 2020 | 0.1 | 15.25 | 21.24 | 1.9 |

DPA = Dipicolinic acid
HEDP = Hydroxyethanediphosphonic acid
*) all concentration data refer to 100% active substance Examples E6 to E11

5 wt. % strength equilibrium peracetic acids containing different hardness stabilizers (examples 6 to 8) and also the same hardness stabilizers combined with an anionic surfactant (examples 9 to 11) were prepared; see Table 5. The solutions were prepared by mixing 28.05 wt. % of $H_2O_2$ (calculated 100%), 9.07 % acetic acid (calculated 100%), 0.97% $H_2SO_4$ (=catalyst), 0.05% dipicolinic acid (=stabilizer), the amounts of hardness stabilizer and surfactant given in the Table and making up to 100% with water. The mixtures were stored in glass bottles and analysed after 5 and 42 days. The concentrations of PAA, $H_2O_2$ and AO are given in Table 5.

Measuring the loss of active oxygen (AO) showed that samples with Sokolan CP 10S™ (BASF AG), a hardness stabilizer in accordance with (ii), had the highest storage stability. The carboxyl groups in hardness stabilizer Belgard EV™ (Ciba Geigy AG), a hardness stabilizer in accordance with (iv), react to a considerable extent with hydrogen peroxide to give percarboxyl groups; this results in the high PAA value in example 8. Surprisingly, this peracid production is largely hindered by the presence of surfactant; see example 11. (The wt. % data in the table include all percarboxylic acid groups, but they were calculated as if they were peracetic acid).

TABLE 5

| No. | Additive and amounts (wt. %) in peracetic acid | Appearance | PAA (wt. %) after 5 days | $H_2O_2$ (wt. %) after 5 days | AO (wt. %) after 5 days | PAA (wt. %) after 42 days | $H_2O_2$ (wt. %) after 42 days | AO (wt. %) after 42 days | AO - difference (wt. %) |
|---|---|---|---|---|---|---|---|---|---|
| E6 | 3% POC 2020 | clear | 4.62 | 25.95 | 13.17 | 4.81 | 25.48 | 12.97 | −0.20 |
| E7 | 3% Sokolan CP 10S *) | cloudy | 4.50 | 26.35 | 13.32 | 4.96 | 25.82 | 13.18 | −0.14 |
| E8 | 3% Belgard EV **) | yellow | 20.72 | 19.15 | 13.36 | 19.90 | 18.16 | 12.71 | −0.65 |
| E9 | 3% POC 2020 + 1% SAS 30 ***) | clear | 4.48 | 26.09 | 13.22 | 5.31 | 25.35 | 13.04 | −0.16 |
| E10 | 3% Sokolan CP 10S + 1% SAS 30 | cloudy | 4.26 | 26.11 | 13.20 | 5.01 | 25.60 | 13.10 | −0.06 |
| E11 | 3% Belgard EP + 1% SAS 30 | yellow | 4.63 | 26.20 | 13.16 | 4.49 | 25.47 | 12.91 | −0.37 |

*) modified polyacrylic acid from BASF AG, $M_w$ = 4000
**) polymer of maleic acid from Giba-Geigy AG, $M_w$ 800–1000
***) sec. alkane sulfonate from Hoechst AG
All concentration data refer to 100% active substance Examples E12 to E17

Determination of the lime-bonding capacity (LBC) of 15 wt. % strength equilibrium peracetic acid (E-PAA 15) containing different hardness stabilizers (examples 12 to 14) as well as hardness stabilizers combined with an anionic surfactant (examples 15 to 17). Table 6 gives the compositions and the lime-bonding capacity in mg of $CaCO_3$ per g of hardness stabilizer, determined by means of turbidity titration. It shows that the LBC is greatly decreased by the presence of an anionic surfactant.

TABLE 6

| No. | Additive in E-PAA 15 | Lime-bonding capacity (mg $CaCO_3$/g) after 88 days storage |
|---|---|---|
| E12 | 3% POC 2020 | 2560 |
| E13 | 3% Sokolan CP 10S*) | 3170 |
| E14 | 3% Belgard EP**) | 1820 |
| E15 | 3% POC 2020 + 1% SAS 30***) | 830 |
| E16 | 3% Sokolan CP 10S + 1% SAS 30 | 1650 |
| E17 | 3% Belgard EV + 1% SAS 30 | 990 |

*) modified polyacrylic acid from BASF AG, $M_w$ = 4000
**) polymer of maleic acid from Ciba-Geigy AG, $M_w$ 800–1000
***) sec. alkane sulfonate from Hoechst AG All concentration data refer to 100% of active substance

What is claimed is:

1. A storage-stable hardness-stablizing percarboxylic acid solution comprising:
   1 to 15 wt. % of one or more percarboxylic acids selected from the group consisting of performic acid and peracetic acid,
   0.1 to 15 wt. % of one or more acids selected from the group consisting of acetic acid and formic acid,
   20 to 50 wt. % of hydrogen peroxide,
   0.1 to 10 wt. % of a hardness stabilizer selected from the group consisting of polymers prepared by the oxidative polymerization of acrolein and polymers prepared by the oxidative polymerization of acrolein and acrylic acid,
   0 to 10 wt. % of one or more additives selected from the group consisting of surfactants, corrosion inhibitors and buffers,
   0 to 3 wt. % of mineral acid,
   0 to 1 wt. % of conventional active oxygen stabilizers and at least 40 wt. % water, wherein the hardness-stabilizer is not cross-linked, the average molecular weight Mw of the hardness stabilizer is in the range 500 to 25000, and some carboxyl groups in the hardness stabilizer may have been converted into percarboxyl groups.

2. A hardness-stabilizing percarboxylic acid solution according to claim 1, wherein the surfactants are anionic or non-ionic surfactants.

3. A hardness-stabilizing percarboxylic acid solution according to claim 1, wherein the mineral acid is sulfuric acid or polyphosphoric acid.

4. A hardness-stabilizing percarboxylic acid solution according to claim 1, comprising peracetic acid and optionally performic acid in a total amount of 0.5 to 6 wt. % as the percarboxylic acid, 1–10 wt. % hardness stabilizers, and 0 to 5 wt. % of anionic surfactants.

5. A hardness-stabilizing percarboxylic acid solution according to claim 1, wherein the hardness-stabilizer has a molecular weight Mw in the range of 1000 to 15000.

6. A hardness-stabilizing percarboxylic acid solution comprising
   0.1 to 15 wt. % of at least one acid selected from the group consisting of peracetic acid and performic acid,
   0.1 to 15 wt. % of at least one acid selected from the group consisting of acetic acid and formic acid,
   20 to 50 wt. % of hydrogen peroxide,
   0 to 10 wt. % of one or more additives selected from the group consisting of surfactants, corrosion inhibitors and buffers,
   0 to 3 wt. % of mineral acid,
   0 to 1 wt. % of conventional active oxygen stabilizers,
   at least 40 wt. % water, and 0.1 to 10 wt. % of one or more hardness stabilizers comprising polymers prepared by oxidative polymerization of acrolein or of acrolein and acrylic acid, or an aqueous solution of said one or more hardness stabilizers added to an aqueous equilibrium peracetic acid solution with a concentration of 0.5 to 2 wt. % of peracetic acid and 40 to 50 wt. % of hydrogen peroxide, wherein said hardness stabilizing percarboxylic acid solution comprises formic acid in an amount of 1 to 6 wt. %, with respect to the polymer, and wherein the hardness-stabilizer is not cross-linked, has an average molecular weight Mw in the range of 500 to 25000, and some carboxyl groups in the hardness stabilizer may have been converted into percarboxyl groups.

7. A hardness-stabilizing percarboxylic acid solution according to claim 6, wherein the hardness-stabilizer has a molecular weight Mw in the range of 1000 to 15000.

* * * * *